United States Patent [19]

Jako

[11] Patent Number: 4,503,854
[45] Date of Patent: Mar. 12, 1985

[54] LASER SURGERY

[76] Inventor: Geza J. Jako, 169 E. Emerson St., Melrose, Mass. 02176

[21] Appl. No.: 504,940

[22] Filed: Jun. 16, 1983

[51] Int. Cl.³ .................................................. A61B 17/38
[52] U.S. Cl. ..................... 128/303.1; 128/395
[58] Field of Search ........ 128/303.1, 303.14, 395–398; 219/121 LS

[56] References Cited

U.S. PATENT DOCUMENTS

| | | | |
|---|---|---|---|
| 3,487,835 | 1/1970 | Koester et al. | 128/303.1 |
| 3,528,424 | 9/1970 | Ayres | 128/303.1 |
| 3,566,872 | 3/1971 | Draeger | 128/303.1 |
| 3,642,007 | 2/1972 | Roberts et al. | 128/395 |
| 3,659,613 | 5/1972 | Bredemeier | 128/303.1 |
| 3,769,963 | 11/1973 | Goldman et al. | 128/2 R |
| 3,796,220 | 3/1974 | Bredemeier | 128/303.1 |
| 3,865,113 | 2/1975 | Sharon et al. | 128/303.1 |
| 3,865,114 | 2/1975 | Sharon | 128/303.1 |
| 3,910,276 | 10/1975 | Polanyi et al. | 128/303.1 |
| 3,930,504 | 1/1976 | de Faforcade | 128/303.1 |
| 4,009,823 | 1/1978 | Isakov et al. | 128/303.1 |
| 4,091,814 | 5/1978 | Togo | 128/303.1 |
| 4,170,997 | 10/1979 | Pinnow et al. | 128/395 |
| 4,174,154 | 11/1979 | Kawasaki | 350/299 |
| 4,215,694 | 8/1980 | Isakov et al. | 128/303.1 |
| 4,289,378 | 9/1981 | Remy et al. | 128/303.1 X |
| 4,309,998 | 1/1982 | Rosa et al. | 128/303.1 |
| 4,408,602 | 10/1983 | Nakajima | 128/303.1 |

OTHER PUBLICATIONS

Jako et al., "Carbon Dioxide Laser Microsurgery . . . ", Transactions, Laser 77, Munchen, Jun. 1977.
Jako, Geza J., "The Use of Lasers in Cancer Surgery".
Jako, Geza J., "Large Operating Room Systems", The Biomedical Laser; Technology and Clinical Applications, 1981, pp. 184–185.
Jako, Geza J., "An Improved Ceiling Mounted Operating Room Laser System", abstract Laser-Tokyo, 1981, pp. 17–30.
Jako, Geza J., "Laser Surgery of the Vocal Cords", The Laryngoscope, vol. 82, Dec. 1972.

Primary Examiner—Edward M. Coven
Attorney, Agent, or Firm—Charles Hieken

[57] ABSTRACT

A laser surgical system for use in the operating room is suspended on the ceiling and can be moved horizontally in an X-Y direction. The system has the laser tubes, power supplies and cooling unit in the suspended assembly. A carbon dioxide laser for cutting and a neodymium YAG laser for coagulation excite a common optical channel. A third laser argon, or other wavelength, can be added to the system. The common optical channel couples the laser beams to an articulate arm delivery system, or a microscope micromanipulator delivery system or fiberoptics delivery system. The microscopic micromanipulator delivery system is motorized so it can be easily moved in any direction. This motorized system is also compatible with a microprocessor for automated surgery. The system also has a built-in digital television system for demonstration, recording or as a robotic eye for association wtih a computer that may help control the laser surgery.

19 Claims, 3 Drawing Figures

LASER SURGERY

The present invention relates in general to laser surgery and more particularly concerns novel apparatus and techniques for performing a wide variety of surgical procedures in an operating room with precision and reduced trauma for patients while facilitating observation and recordation through the use of laser sources of different wavelengths transmittable to a patient over a common optical path that is also observable by the surgeon.

As an example of prior art laser surgical apparatus reference is made to U.S. Pat. Nos. 3,487,835, 3,528,424, 3,642,007, 3,659,613, 3,769,963, 3,796,220, 3,865,113, 3,865,114, 3,910,276, 4,069,823, 4,170,997 and 4,174,154.

It is an important object of this invention to provide an improved laser surgical system.

According to the invention, there is means defining a common optical path for exchanging optical energy with a patient on an operating table, at least first and second laser sources of different wavelength, means for coupling the first and second laser sources to the common optical path for allowing simultaneous delivery of optical energy from the first and second laser sources of the different wavelengths over the common optical path, and means for selectively positioning the common optical path. Preferably, there is optical observing means, such as a microscope, and means for coupling the optical observing means to the common optical path for allowing a surgeon to directly observe through the optical observing means the region of a patient upon which laser energy may act. Preferably the apparatus is suspended over the operating table from rails that facilitate X-Y movement in the horizontal plane, and the common optical path comprises a telescoping assembly that allows movement in the Z direction. The system may include vents, an aspirator and a fiberoptic lighting system for illuminating with sterile disposable plastic covers. Preferably one of the laser sources is a carbon dioxide laser for cutting and a second is a neodymium YAG laser for coagulation, or evaporation.

Numerous other features, objects and advantages of the invention will become apparent from the following specification when read in connection with the accompanying drawing in which.

Figure 1:
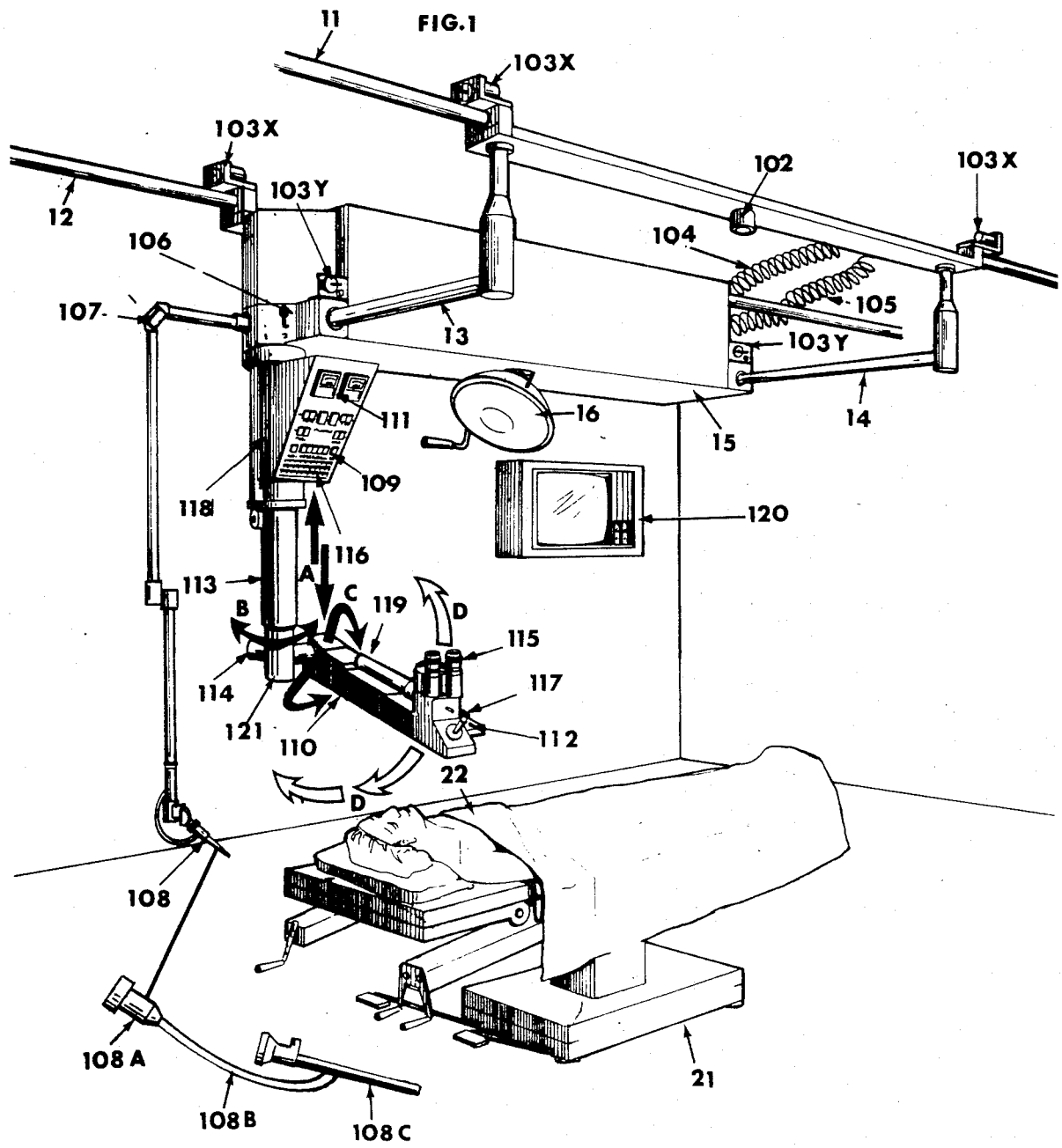
FIG. 1 is a perspective view of an embodiment of the invention in an operating room.

With reference now to the drawing and more particularly FIG. 1 thereof, there is a shown a perspective view of a multipurpose multiwavelength surgical laser system suspended from X rails 11 and 12 and Y rails 13 and 14. X rails 11 and 12 support Y rails 13 and 14 which support housing 15. Housing 15 includes the lasers with associated power supplies, controllers and cooling systems and supports accessory operating room light 16 and other elements in the system positionable in X, Y and Z as described below. A stationary column 118 depends from housing 15 and accommodates telescoping column 113 comprising a common optical path for transmitting energy from a laser source and allowing the surgeon to observe the incision. A motor (not shown) may provide mechanical energy for lowering and raising the telescoping structure 113 as indicated by arrows A in accordance with well-known techniques, not described in detail herein to avoid obscuring the principles of the invention, when actuated by an appropriate control button on switch pad 112 to provide Z-axis positioning.

A microscopic delivery system arm 110 selectively angularly displaced about its fixed end by motor 114, as indicated by arrows D—D, and manually rotatable about vertical and horizontal axes, as indicated by arrows B and C, is carried by and optically coupled to end section 121 and includes a microscope 115 with variable magnification. A switch pad 112 controls motor 114 to selectively raise and lower the delivery arm 110 with fine and coarse adjustment in accordance with well-known techniques. Switch pad 112 may be used to effect X-Y positioning of the apparatus by releasing brakes, such as 102, to allow manual movement. Electromechanical brake 102, which may be of conventional type, mechanically grasps the rail 11 when deenergized, and the solenoid acts against a spring when a solenoid is energized to release the brake and allow movement, thereby normally keeping the assembly stationary for observation and/or cutting, and/or coagulating. The brakes for rails 13 and 14 are not visible in FIG. 1 and are in cabinet 15. Air piston shock absorbers, such as 103X and 103Y, cushion the chock when the assembly reaches the ends of a pair of rails.

A television camera 119 provides a television signal of what is observed through microscope 115 for display on television monitor 120 and may also deliver this signal to a hard copy printer or video recorder system for recording. Television camera 119 may also comprise a robotic eye when the invention is used in connection with an automatic control system to, for example, guide and control the cutting laser along a predetermined path.

The invention may also include an articulated arm delivery system 107 terminating in a hand piece coupler assembly 108 which may be used by a surgeon in a manner analogous to a scalpel, while using laser energy not only for cutting, but also for coagulating. A hand piece may be coupled to system 107 by a short fiberoptics coupler. This coupling arrangement is shown magnified as optical input jack 108A, fiberoptic cable 108B and endoscope 108C.

The apparatus is suspended above an operating table 21 above a patient 22 where it may be conveniently controlled by a surgeon having access to control panel 109, microscope 115, joystick 117 with a trigger switch on its end and/or a footswitch (not shown) and switch pad 112. Actuating the trigger switch or footswitch typically operates shutter A or B (FIG. 3) to allow laser energy from an associated laser to enter the common optical path as described below. Keyboard 116 on control panel 109 may be used to enter appropriate commands for CW and/or pulsed operation of the lasers or other information when the apparatus is used in connection with a computer. Meters 111 indicate appropriate power level operating information, or laser potentials and/or currents.

An optical switch 106 allows manual direction of laser energy selectively into the telescoping assembly below or the articulated arm 107. Power cables 104 provide electrical power to the lasers and associated equipment in housing 15. Water hoses 105 provide water for cooling.

Figure 2:
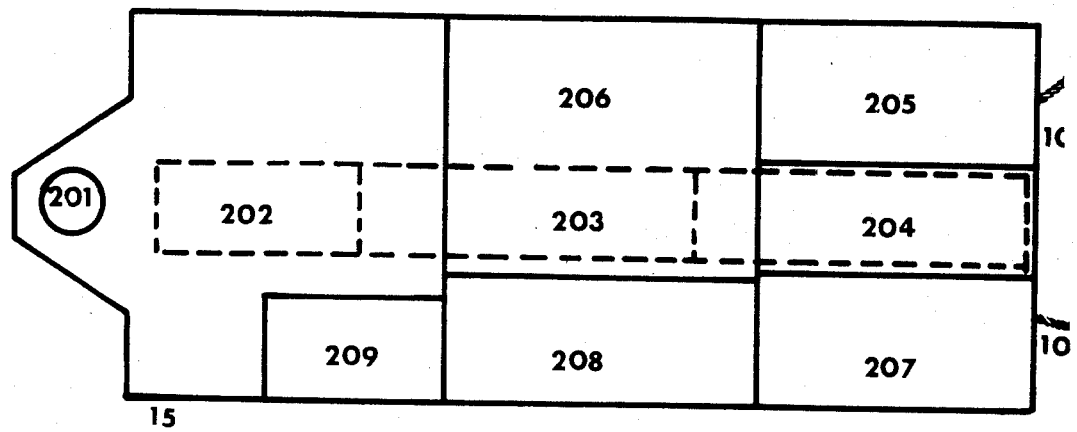
FIG. 2 is a diagrammatic plan view of an embodiment of the invention illustrating the location of various system components.

Referring to FIG. 2, there is shown a diagrammatic representation of units in housing 15. Housing 15 may include an aiming laser with power supply 202, carbon dioxide laser 203, cooling package 205 and 207, carbon dioxide laser power supply 206, neodymium YAG laser 204, neodymium YAG laser power supply 208 and a conventional control unit 209, containing relays, interlocks, circuit breakers, controls for the operating modes of the lasers and the like. Optical port 201 admits laser beam energy to the telescope below.

Figure 3:
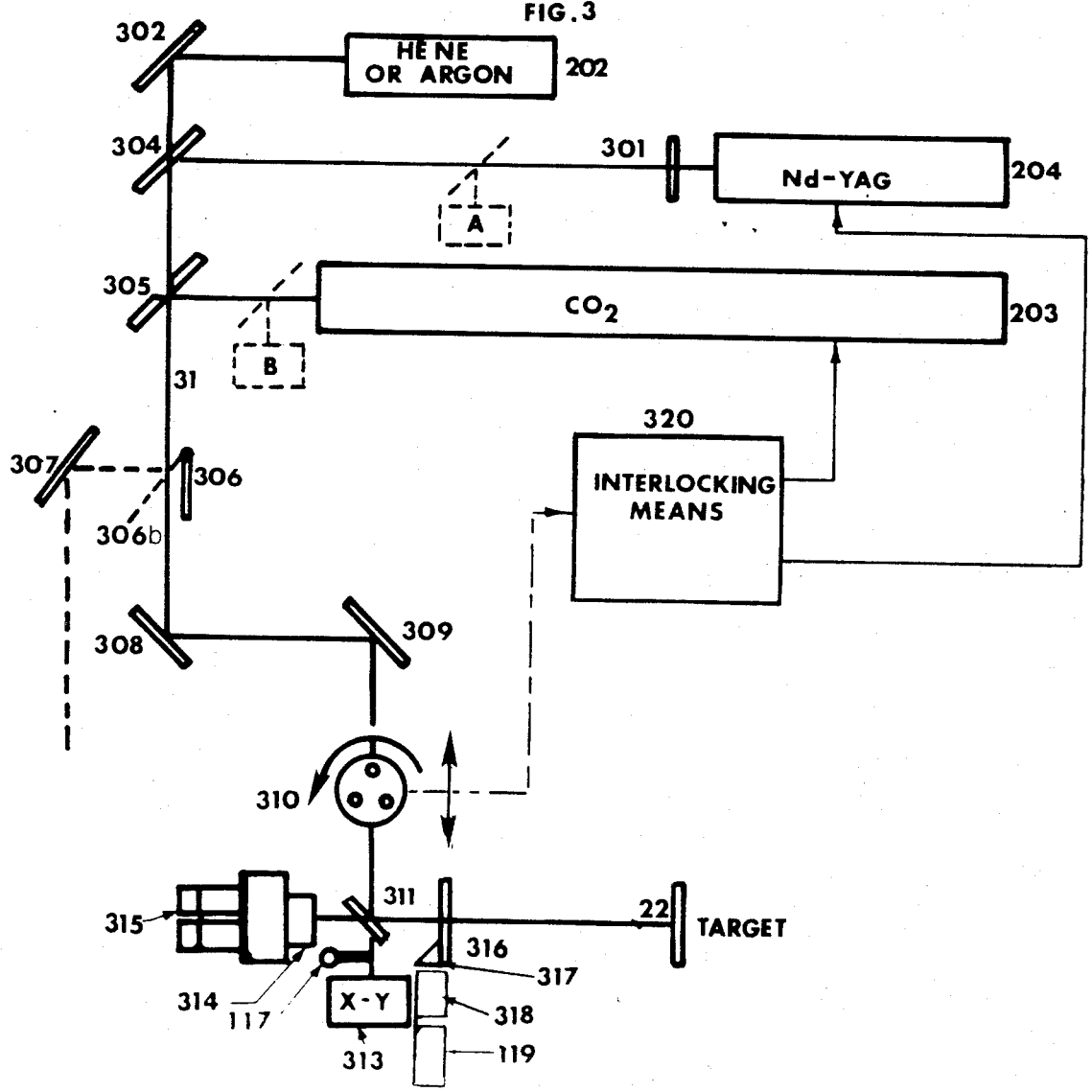
FIG. 3 is a diagrammatic representation of an exemplary optical system according to the invention helpful in understanding how the different optical signals enter the common optical path.

Referring to FIG. 3, there is shown a diagrammatic representation of the optical system according to the invention. HeNe or Argon laser 202 illuminates a 45° reflector 302 that deflects the beam along the axis 31 of the telescoping section below through coated mirrors 304 and 305. Coated mirror 304 receives the laser beam from neodymium YAG laser 204 through focusing lens 301. Perforated mirror 305 receives the laser beam from $CO_2$ laser 203. With reflecting mirror 306 actuated by switch 106 (FIG. 1) positioned as shown, 45° coated mirrors 308 and 309 deflect one or more active beams through focusable turret 310 upon movable mirror 311 and through perforated collimating lens 316 of the microscope to patient 22. Turret 310 includes three lenses; one for $CO_2$ laser and aiming light, the second for Nd-YAG laser and aiming light, and the third a compromise for all wavelengths. The first two are interlocked by interlocking means 320 so that only the associated laser can operate when a respective lens is positioned along the common optical path. The surgeon may then observe through microscope 315 the effect of the laser on the patient while controlling its position with joystick 117. The perforation on axis of lens 316 passes the laser beam freely while the remaining portion acts as a collimating lens for viewing and recording. The microscope may also include an indicator for power output, lasers then being used and interlock indicator.

Electromechanical shutters A and B intercept the outputs of Nd-YAG and $CO_2$ lasers 204 and 203 respectively with a 45° mirror to also function as a heat sink power meter element when positioned as shown in accordance with well-known techniques.

With reflecting mirror 306 positioned as represented by dotted line 306b, the active laser beam is directed upon reflecting mirror 307 into articulated arm delivery system 107.

Joystick 117 moves mirror 311 to facilitate aiming the beam where desired. Alternatively, X-Y controller 313 preferably includes stepping motors for positioning mirror 311. Optics 314 preferably includes an interlocked protective optic filter interposed when Nd-YAG laser 204 or other high power laser is being used.

Television camera 119 preferably receives an optical image of the area of the patient being treated surgically through a 45° prism 317 and zoom lens 318 of a known type not described in detail to avoid obscuring the principles of the invention.

The invention has a number of advantages. It provides a multipurpose multiwavelength laser system having the flexibility to deliver one or more beams under precise convenient practical control of the operating surgeon while being compatible with computer operation. It may be installed in a dedicated operating room that allows the surgeon to develop new procedures where in whole, or in part, the laser surgical system may be used to achieve more precision and less invasive surgery. The invention is also compatible with diagnostic instrumentation having computer storage in which stored diagnostic information may be processed for automatic or semiautomatic surgery. Then, suitable stepping motors or other drives may be included for controlling movement along directions B and C as well as A and D. For example, information of a CAT scan or NMR of the patient in computer storage may be processed and utilized to assist the surgeon in removing tissue more uniformly and speedily.

It is evident that those skilled in the surgical and other technical arts may now make numerous uses and modifications of and departures from the specific apparatus and techniques described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. Laser surgery apparatus comprising,
   at least first and second laser sources of optical energy at different wavelengths for providing operating and aiming laser beams respectively,
   means defining a common optical path for exchanging optical energy with a patient at the patient end of said path,
   means including at least one perforated mirror for coupling said laser sources to said common optical path for allowing simultaneous delivery of optical energy from said first and second laser sources of said different wavelengths over said common optical path to said patient end,
   and means for simultaneously moving said aiming and operating laser beams together over a region at said patient end.

2. Laser surgery apparatus in accordance with claim 1 and further comprising,
   microscope means having its optical axis oriented along a portion of said common optical path and coupled to said means defining a common optical path for allowing a surgeon to directly observe through said microscope means the region of a patient upon which laser energy may act.

3. Laser surgery apparatus in accordance with claim 2 wherein said microscope means comprises,
   perforated lens means formed with a small perforation embracing said common optical axis for passing a beam of laser energy therethrough while converging optical rays from said region of a patient.

4. Laser surgery apparatus in accordance with claim 2 and further comprising,
   articulated arm means having a hand piece for delivering optical energy to a patient under hand control of a surgeon,
   and optical switching means in said common optical path for selectively diverting optical energy from said common optical path to said articulated arm means in a first position and to said microscope means in a second position.

5. Laser surgery apparatus in accordance with claim 4 and further comprising,
   fiberoptic coupling means for coupling optical energy from said articulated arm means to said hand piece.

6. Laser surgery apparatus in accordance with claim 2 and further comprising control means in proximity to said microscope means for enabling a surgeon to control movement of said laser energy upon said patient.

7. Laser surgery apparatus in accordance with claim 6 wherein said control means comprises joystick means coupled to a reflecting mirror in said optical path for selectively positioning said mirror.

8. Laser surgery apparatus in accordance with claim 7 and further comprising,
a source of aiming optical energy and means for coupling the latter source to said common optical path for providing an aiming beam for illuminating said patient corresponding to the intersection of said common optical path with said patient to allow a surgeon to selectively position said common optical path to establish its intersection with said patient at a predetermined region where laser treatment is desired.

9. Laser surgery apparatus in accordance with claim 7 and further comprising,
trigger switch means on said joystick means for selectively controlling the flow of energy over said common optical path.

10. Laser surgery apparatus in accordance with claim 1 and further comprising,
a source of aiming optical energy and means for coupling the latter source to said common optical paths for providing an aiming beam for illuminating said patient corresponding to the intersection of said common optical path with said patient to allow a surgeon to selectively position said common optical path to establish its intersection with said patient at a predetermined region where laser treatment is desired.

11. Laser surgery apparatus in accordance with claim 1 wherein said first laser source comprises a laser from the group consisting of a $CO_2$ laser and Nd-YAG laser.

12. Laser surgery apparatus in accordance with claim 11 wherein said second laser source comprises a laser from the group consisting of helium-neon and argon lasers.

13. Laser surgery apparatus in accordance with claim 1 and further comprising,
a housing supporting said first and second laser sources,
said means defining a common optical path comprising means suspended from said housing,
and overhead suspension means for supporting said housing and allowing selective displacement thereof in orthogonal directions in the horizontal plane.

14. Laser surgery apparatus in accordance with claim 1 and further comprising,
television camera means coupled to said common optical path for providing a video signal representative of the observed region of a patient upon which laser energy transmitted on said common optical path may act.

15. Laser surgery apparatus in accordance with claim 14 and further comprising,
microscope micromanipulator means having its optical axis oriented along a portion of said common optical path and coupled to said means defining a common optical path for allowing a surgeon to observe through and control with said microscope micromanipulator means the region of a patient upon which laser energy may act,
said microscope micromanipulator means carrying said television camera means.

16. Laser surgery apparatus comprising,
at least first and second laser sources of optical energy at different wavelengths,
means defining a common optical path for exchanging optical energy with a patient,
means for coupling said laser sources to said common optical path,
focusable turret lens means in said common optical path having a first lens selectively positionable in said common optical path for focusing energy from said first laser source,
second lens means selectively positionable in said common optical path for focusing energy from said second laser source,
and third lens means selectively positionable in said common optical path for focusing energy at a plurality of optical wavelengths.

17. Laser surgery apparatus in accordance with claim 15 and further comprising,
interlocking means associated with said first and second lens means for allowing said first laser source and said second laser source to provide energy over said common optical path only when said first and second lens means respectively are positioned in said common optical path.

18. Laser surgery apparatus comprising,
at least a first laser source,
means defining a common optical path for exchanging optical energy with a patient,
means for coupling said laser source to said common optical path,
and microscope means having its optical axis oriented along a portion of said common optical path and coupled to directly said means defining a common optical path for allowing a surgeon to observe through said microscope means the region of a patient upon which laser energy may act,
said microscope means comprising perforated lens means formed with an opening embracing said common optical path for passing a beam of laser energy therethrough while focusing optical energy from said region of a patient.

19. Laser surgery apparatus in accordance with claims 17 or 3 wherein said first laser source comprises a $CO_2$ laser and said second laser source comprises a Nd-YAG laser.

* * * * *